US007205282B1

(12) United States Patent
Hirabayashi et al.

(10) Patent No.: US 7,205,282 B1
(45) Date of Patent: Apr. 17, 2007

(54) REMEDIES FOR HEPATITIS

(75) Inventors: Kazuko Hirabayashi, Kyoto (JP); Junzo Seki, Ibaraki (JP)

(73) Assignee: Nippon Shinyaku Co., Ltd., Kyoto (JP)

( * ) Notice: Subject to any disclaimer, the term of this patent is extended or adjusted under 35 U.S.C. 154(b) by 0 days.

(21) Appl. No.: 09/646,135

(22) PCT Filed: Mar. 23, 1999

(86) PCT No.: PCT/JP99/01438

§ 371 (c)(1),
(2), (4) Date: Sep. 8, 2000

(87) PCT Pub. No.: WO99/48531

PCT Pub. Date: Sep. 30, 1999

(30) Foreign Application Priority Data

Mar. 24, 1998 (JP) .................................. 10-076055

(51) Int. Cl.
*A61K 31/70* (2006.01)
*A01N 43/04* (2006.01)

(52) U.S. Cl. ........................................................ 514/44
(58) Field of Classification Search .................. 514/44; 435/417, 450, 455
See application file for complete search history.

(56) References Cited

U.S. PATENT DOCUMENTS 4,140,761 A * 2/1979 Gerin et al. ................ 424/85.5
5,049,386 A    9/1991 Eppstein et al. ............. 424/427
5,298,614 A * 3/1994 Yano et al. ................. 536/25.5

FOREIGN PATENT DOCUMENTS

EP    0685 457 A1    2/1994
EP    0 685 234 A1   12/1995
EP    1 029 544 A1   10/1998

OTHER PUBLICATIONS

NN Zein, Cytokines Cell Mol Ther., "Interferons in the management of viral hepatitis," Dec. 1998,4(4):229-241, Abstract Only.*
L Ferrell, Pathology, "Liver Pathology:Cirrhosis, Hepatitis, and Primary Liver Tumors," 2000, vol. 13, No. 6, pp. 679-704.*
K hirabayashi et al., Cancer Research,"Inhibition of Cancer Cell Growth by Polyinosinic-Polycytidylic Acid/Cationic Liposome Complex:A New Biological Activity," Sep. 1999, 59, pp. 4325-4333.*
RI Mahato et al., Human Gene Therapy, "Biodistribution and Gene Expression of Lipid/Plasmid Complexes after Systemic Administration," Sep. 1998, 9: 2083-2099.*
JP Wong et al., Vaccine, "Liposome-mediated immunotherapy against respiratory influenza virus infection using double-stranded RNA poly ICLC," Mar. 1999, 17, pp. 1788-1795.*
RI Magato et al., Journal of Pharmaceutical Sciences, "Physicochemical and Pharmacokinetic Characteristics of Plasmid DNA/Cationic Liposome Complexes," Nov. 1995, vol. 84, No. 11, pp. 1267-1271.*
A Mountain, Trends Biotechnol., "Gene therapy: the first decade," Mar. 2000, vol. 18, pp. 119-128.*
WF Anderson, Nature, "Human gene therapy," Apr. 1998, vol. 392, pp. 25-30.*
IM Verma et al., Nature, "Gene therapy-promises, problems and prospects," Sep. 1997, vol. 389, pp. 239-242.*
Wooley et al., American Journal of Veterinary Research, vol. 35, pp. 267-273, 1974.*
Machida et al., Japan J. Microbiol. vol. 20, pp. 71-76, 1976.*
Liaw, J Gastroenterol Hepatol. Oct. 1997;12(9-10):S346-53.*
Desmyter et al. Texas Reports on Biology and Medicine 35:516-522, 1977.*
Bever et al. Journal of Interferon Research, 5: 423-428, 1985.*
Black et al. Antimicrobial agents and chemotherapy, 3:198-206, 1973.*
Tytell et al. Proc. Soc. Exp. Biol. Med. 135 :917-21, 1970.*
A Comparison of Negatively and Positively Charged Liposomes Containing Entrapped Polyinosinic Polycytidylic Acid For Interferon Induction in Mice; Wayne E. Magee, Martin L. Talcott, Steven X. Straub and Catherine Y. Vriend; May 26, 1976; pp. 610-618.
Database Medline 'Online! Jun. 1994 "In vivo antiviral effects of mismatched double-strandded RNA on duck hepatitis B virus."
Banerjee, R., et al "Selective Inhibition of Hepatitis B Virus and Human Immunodefiency Virus Sequence-Promoted Gene Expression by Cotransfected Poly(I):Poly(C)", Virology, Raven Press, New York, NY U.S. vol. 179, 1990, pp. 410-415 XP002918244.

* cited by examiner

*Primary Examiner*—Brian Whiteman
(74) *Attorney, Agent, or Firm*—Greenberg Traurig LLP; Gerard F. Diebner

(57) ABSTRACT

The object of the present invention is to provide a novel medicinal agent useful in the treatment or the prevention of hepatitis.

The present invention is, for example, a therapeutic or preventive agent for hepatitis characterized in that it comprises a complex of a drug carrier consisting essentially of 2-O-(2-diethylaminoethyl)-carbamoyl-1,3-O-dioleoylglycerol and a phospholipid with poly(I).poly(C).

2 Claims, 2 Drawing Sheets

REMEDIES FOR HEPATITIS

TECHNICAL FIELD

The present invention relates to a therapeutic agent for hepatitis.

As used in this specification, the code "I" stands for inosinic acid, "C" for cytidylic acid, "A" for adenylic acid, and "U" for uridylic acid.

The terms "mismatched poly(I).(C) and mismatched poly (A).poly(U) mean th at poly(I).(C) and poly(A).poly(U) have double-stranded nucleic acid bases containing partly non-complementary nucleic acid, as well known in the art.

BACKGROUND ART poly(I).(C) is a double-stranded RNA consisting of polyinocinic acid and polycytidylic acid is broadly known to be a medicinally active substance having interferon-inducing activity and immunopotentiating activity.

It has recently been reported that interferon itself is effective in the treatment of hepatitis C (e.g., KAN-TAN-SUI, 9(4), 611 (1984); ibid., 13(1), 123 (1986); ibid., 12(5), 809 (1986); ibid., 23(5), 1065 (1991)). It is, however, difficult to treat hepatitis C with poly(I).poly(C) capable of inducing interferon just by conventional administration methods, in view of the extent of interferon induction, toxicity, and the like.

On the other hand, there are known pharmaceutical- or drug-carriers including those generally called cationic liposomes such as LIPOFECTIN (registered trademark) and those composed of a glycerol derivative such as 2-O-(2-diethylaminoethyl)carbamoyl-1,3-O-dioleoylglycerol of the following chemical formula [I] and a phospholipid as essential components [e.g. PCT WO91/17424, PCT WO94/19314].

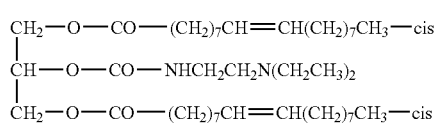

[I]

The cationic liposome is considered to be a small vesicle composed of lipid bimolecular layer and charged positively in an aqueous solution. Since a cationic liposome becomes positively charged while a double-stranded RNA such as poly(I).poly(C) negatively charged in an aqueous solution, a cationic liposome and poly(I).poly(C), for instance, may easily form a complex when subjected to a typical dispersing treatment.

However, it is not known at all whether a complex of a double-stranded RNA such as poly(I).poly(C) with a drug carrier like the above-mentioned cationic liposome would be effective in the treatment of hepatitis and the like.

DISCLOSURE OF INVENTION

The object of the present invention is to provide a novel medicinal agent useful in the treatment or the prevention of hepatitis.

The inventors of the present invention have found for the first time that a complex of a double-stranded RNA such as poly(I).poly(C) with a drug carrier like cationic liposomes are accumulated specifically in the liver and spleen and can induce interferon effective in the treatment of hepatitis etc. for a long time, and have established the present invention.

The present invention, in one aspect, provides a therapeutic or preventive agent for hepatitis (hereinafter, referred to as "the agent of the present invention") characterized in that it comprises a complex of a double-stranded RNA such as poly(I).poly(C) with a cationic liposome. The complex will hereinafter be referred to as "the complex".

The present invention will be described in detail below.

The cationic liposome usable in the present invention includes LIPOFECTIN (registered trademark), LIPOFECTAMINE (registered trademark), LIPOFECTACE (registered trademark), DMRIE-C (registered trademark), or a drug carrier disclosed in PCT WO94/19314, e.g., the one composed of 2-O-(2-diethylaminoethyl)carbamoyl-1,3-O-dioleoylglycerol of the above-mentioned chemical formula [I] (hereinafter, referred to as "Compound A") and a phospholipid as essential components.

Examples of the preferred cationic liposome for the present invention include a drug carrier made from Compound A and a phospholipid, as essential components. The resultant drug carrier will hereinafter be referred to as "the carrier".

Examples of a double-stranded RNA usable in the present invention include poly(I).poly(C), mismatched poly(I).poly (C), poly(A).poly(U), mismatched poly(A).poly(U). Among them, the poly(I).poly(C) is suitable.

The chain length of the above-mentioned double-stranded RNA is not particularly restricted, but it is suitable to be within the range of 50–2,000 base pairs (bp), preferably, 100 to 500 bp, more preferably, 200–400 bp. If the chain length of RNA is less than 50 bp, effectiveness would be insufficient, and if it is over 2,000 bp, the safety would be questionable. The chain length ranging from 100 bp to 500 bp is considered to be balanced range in connection with efficacy and safety. Likewise, as for the length of poly(I).poly(C), 100–500 bp is preferred and 200–400 bp is still more preferred. Since the double-stranded RNA like poly (I).poly(C), etc. usually exists with a given distribution of various chain lengths, the above-mentioned chain length indicates the base pair numbers of the largest distribution and is herein referred to as "mean chain length".

The phospholipid in the carrier is not particularly restricted provided that it is a pharmaceutically acceptable. Nonrestrictive examples of phospholipid include phosphatidylcholine, phosphatidylethanolamine, phosphatidylinositol, phosphatidylserine, sphingomyelins, and lecithin. Hydrogenated phospholipids can also be used. The preferred phospholipid includes egg yolk phosphatidylcholine, egg yolk lecithin, soybean lecithin, and egg yolk phosphatide. Two or more different phospholipids can also be used in combination. As to phospholipids to be used with Compound A, phosphatidylcholine and lecithin are superior to phosphatidylethanolamine which is commonly used in the cationic liposome.

In a preferred embodiment, the present invention provides a pharmaceutical preparation comprising a complex of the carrier wherein the phospholipid is lecithin and a poly(I).poly(C) having a mean chain length ranging from 100 to 500 bp, especially 200 to 400 bp.

The ratio of the cationic liposome to the double-stranded RNA varies depending on the kind or chain length of cationic liposome or double-stranded RNA, the type or stage of hepatitis, and other factors, but the recommended proportion of the double-stranded RNA relative to 10 weight parts of the cationic liposome is 0.05–10 weight parts, preferably 0.1–4 weight parts, and more preferably 0.5–2 weight parts. Likewise, the recommended proportion of poly(I).poly(C) relative to 10 weight parts of the carrier is 0.05–10 weight parts, preferably 0.1–4 weight parts, and more preferably 0.5–2 weight parts.

The ratio of Compound A to the phospholipid in the carrier varies depending on the kind, chain length, and amount of double-stranded RNA and the kind of phospholipid, and other factors, but the recommended proportion of phospholipid relative to each weight part of Compound A is 0.1–10 weight parts, preferably 0.5–5 weight parts, and more preferably 1–2 weight parts.

The agent of the present invention may, for example, be provided in the form of liquid preparation for injection or drip infusion, in which the complex is dispersed in an aqueous solution, or in the lyophilized form. In the case of a liquid preparation, the recommended concentration of the complex is 0.001–25% (w/v), preferably 0.01–5% (w/v), and more preferably 0.1–1% (w/v).

The agent of the present invention may contain any of pharmaceutically acceptable additives, such as an auxiliary emulsifier, stabilizer, isotonizing agent, and/or a pH regulator, in suitable amounts. Specific examples include auxiliary emulsifiers such as $C_{6-22}$ fatty acids (e.g. caprylic acid, capric acid, lauric acid, myristic acid, palmitic acid, stearic acid, oleic acid, linoleic acid, arachidonic acid, docosahexenoic acid) or their pharmaceutically acceptable salts (e.g. sodium salts, potassium salts, calcium salts, etc.), albumin, dextran, etc.; stabilizers such as cholesterol, phosphatidine, etc.; isotonizing agents such as sodium chloride, glucose, maltose, lactose, sucrose, trehalose, etc.; and pH regulator such as hydrochloric acid, sulfuric acid, phosphoric acid, acetic acid, sodium hydroxide, potassium hydroxide, triethanolamine, etc.

The agent of the present invention can, for example, be prepared in a manner similar to the general technology for the production of liposomes. A typical method comprises dispersing a double-stranded RNA such as poly(I).poly(C) with a cationic liposome or raw materials thereof (e.g., Compound A and a phospholipid) in an aqueous solution. Examples of the aqueous solution includes, but is not limited to, water for injection, distilled water for injection, electrolyte solution such as physiological saline, or glucose solution. The dispersing treatment can be performed with a suitable dispersing machine such as a homomixer, homogenizer, ultrasonic disperser, ultrasonic homogenizer, high-pressure emulsifier-disperser, Microfluidizer (trade name), Nanomizer (trade name), Ultimizer (trade name), or Manton-Gaulin high-pressure homogenizer. Further, the dispersing treatment can be divided into several steps including, for example, a crude dispersion step.

A commercially available cationic liposome can be used as it is or after appropriate processing.

When the agent of the present invention is prepared from the raw materials for cationic liposome, the materials and the double-stranded RNA such as poly(I).poly(C) can be dispersed together. Alternatively, the cationic liposome is first formed by dispersing the materials, and then redispersed after the addition of a double-stranded RNA such as poly (I).poly(C) to obtain the agent of the present invention.

The pharmaceutically acceptable additives mentioned above can be added at a suitable stage before or after the dispersion.

The agent of the present invention thus prepared by the dispersing procedure may be freeze-dried to provide a lyophilized agent of the present invention. The freeze-drying operation can be carried out in a conventional manner. For example, the agent of the present invention obtained by dispersing procedure is sterilized and distributed into vials at a determined amount. The filled vials are subjected to preliminary freezing at about −40° C. to −20° C. for about 2 hours and, primary drying in vacuo at about 0° C. to 10° C. and then to secondary drying in vacuo at about 15° C. to 25° C. Generally, the vials are purged with nitrogen gas and stoppered to provide the objective lyophilized agent of the present invention.

The lyophilized agent of the present invention can be generally reconstituted by adding a suitable solvent (for reconstitution) and put to use. The solvent for reconstitution includes water for injection, electrolyte solution such as physiological saline, glucose solution, and other ordinary infusions. The volume of the solvent for reconstitution varies depending on the intended use and is not particularly restricted but may preferably be 0.5–2 times the volume of the agent prior to freeze-drying, or not larger than 500 mL.

The agent of the present invention can accumulate specifically in the liver and spleen, and induce more β-interferon for a long time than a double-stranded RNA such as poly(I).poly(C) alone, and is useful in the treatment or prevention of hepatitis in mammals inclusive of man. Particularly, the agent of the present invention which is related to a complex of the carrier comprising lecithin as a phospholipid with poly(I).poly(C) (mean chain length=100–500 bp, particularly, 200–400 bp) as a double-stranded RNA is highly efficacious and yet is very low in toxicity.

The agent of the present invention can for example be administered intravenously, transmucosally, or into the hepatic artery.

The dosage of the agent of the present invention in hepatitis therapy varies depending on the kinds of double-stranded RNA and phospholipid, the type of hepatitis, the stage of hepatitis, the recipient's age and animal species, route or mode of administration. In terms of double-stranded RNA, the recommended dosage is usually 1 μg–50 mg/man, and preferably 10 μg–10 mg/man per dose. In terms of poly(I).poly(C), the recommended dosage is usually 1 g–50 mg/man, and preferably 10 μg–10 mg/man per dose. The agent of the present invention can be administered in one shot or by drip injection once through 3 times a day, every day, every other day, or on a weekly or fortnightly basis.

BEST MODE FOR CARRYING OUT THE INVENTION

The following working examples and test examples illustrate the present invention in more detail. It should be understood that the concentration of the agent of the present invention is invariably expressed in the concentration of the poly(I).poly(C) in the agent.

EXAMPLE 1

A solution of 40 g of maltose in 100 mL of water for injection was stirred with 2 g of Compound A and 2 g of purified egg yolk lecithin and the mixture was treated with a homogenizer for 5 minutes to prepare a crude carrier dispersion. This crude dispersion was further treated with a bench-top compact emulsifier-disperser for 1 hour and adjusted to 250 mL with water for injection. The resulting carrier dispersion was recovered. To 250 mL of this carrier dispersion was added 150 mL of an aqueous solution containing 500 mg of poly(I).poly(C) [mean chain length: about 200 bp] with stirring, and using a bench-top compact emulsifier-disperser, the mixture was further treated for 1 hour to provide the agent of the present invention. This agent was then distributed into vials, 1 mL per vial, and freeze-dried in a conventional manner to provide a lyophilizate.

EXAMPLE 2

A solution of 4 kg of sucrose in 10 L of water for injection was stirred with 50 g of Compound A and 30 g of egg yolk phosphatide and the mixture was treated with a Manton-Gaulin high-pressure homogenizer for 10 minutes. The resulting dispersion was made up to 25 L with water for injection and recovered. To 20 L of this carrier dispersion was added 12 L of an aqueous solution containing 10 g of poly(I).poly(C) [mean chain length about 200 bp] with stirring, and the mixture was adjusted to pH 5.5 with hydrochloric acid and further treated with a Manton-Gaulin high-pressure homogenizer for 30 minutes to provide the agent of the present invention. This agent was then distributed into vials, 20 mL per vial, and freeze-dried in a conventional manner to provide a lyophilizate. This lyophilized preparation was reconstituted by adding a commercial 5% glucose infusion (500 mL).

EXAMPLE 3

A solution of 20 g of glucose in 100 mL of water for injection was stirred with 2 g of Compound A and 2 g of soybean lecithin and the mixture was treated with a homogenizer for 5 minutes to prepare a crude carrier dispersion. This crude dispersion was further treated with a bench-top compact high pressure emulsifier-disperser for 1 hour and adjusted to 250 mL with water for injection. The resulting carrier dispersion was recovered. To 250 mL of this carrier dispersion was added 150 mL of an aqueous solution containing 50 mg of poly(I).poly(C) [mean chain length: about 200 bp] with stirring, and using a bench-top compact high pressure emulsifier-disperser, the mixture was further treated for 1 hour to provide the agent of the present invention.

EXAMPLE 4

A solution of 40 g of maltose in 100 mL of water for injection was stirred with 1.2 g of Compound A and 2.0 g of purified egg yolk lecithin and this crude dispersion was further treated with a bench-top compact high pressure emulsifier-disperser for 30 minutes and made up to 250 mL with water for injection. The resulting carrier dispersion was recovered. To 250 mL of this carrier dispersion was added 150 mL of an aqueous solution containing 200 mg of poly(I).poly(C) [mean chain length about 200 bp] with stirring, and using a bench-top compact high pressure emulsifier-disperser, the mixture was further treated for 2 hours to provide the agent of the present invention.

EXAMPLE 5

A solution of 40 g of maltose in 100 mL of water for injection was stirred with 1.2 g of Compound A and 2.0 g of purified egg yolk lecithin and this crude dispersion was further treated with a bench-top compact high pressure emulsifier-disperser for 30 minutes and made up to 250 mL with water for injection. The resulting carrier dispersion was recovered. To 250 mL of this carrier dispersion was added 150 mL of an aqueous solution containing 100 mg of poly(I) [mean chain length: 360 base] and 100 mg of poly(C) [mean chain length: 318 base] with stirring, and using a bench-top compact high pressure emulsifier-disperser, the mixture was further treated for 2 hours to provide the agent of the present invention.

EXAMPLE 6

A solution of 40 g of maltose in 100 mL of water for injection was stirred with 2 g of Compound A and 2 g of purified egg yolk lecithin and the mixture was treated with a homogenizer for 5 minutes to prepare a crude carrier dispersion. This crude dispersion further treated with a bench-top compact high pressure emulsifier-disperser for 1 hour and adjusted to 250 mL with water for injection. The resulting carrier dispersion was recovered. To 250 mL of this carrier dispersion was added 150 mL of an aqueous solution containing 250 mg of poly(I) [mean chain length: 1419 base] and 250 mg of poly(C) [mean chain length: 1491 base] with stirring, and using a bench-top compact high pressure emulsifier-disperser, the mixture was further treated for 1 hour to provide the agent of the present invention. This agent was then distributed into vials, 1 mL per vial, and freeze-dried in a conventional manner to provide a lyophilizate.

EXAMPLE 7

A solution of 40 g of maltose in 100 mL of water for injection was stirred with 1.2 g of Compound A and 2.0 g of purified egg yolk lecithin and this crude dispersion was further treated with a bench-top compact high pressure emulsifier-disperser for 30 minutes and made up to 250 mL with water for injection. The resulting carrier dispersion was recovered. To 250 mL of this carrier dispersion was added 150 mL of an aqueous solution containing 100 mg of poly(I) [mean chain length: 84 base] and 100 mg of poly(C) [mean chain length: 76 base] with stirring, and using a bench-top compact high pressure emulsifier-disperser, the mixture was further treated for 2 hours to provide the agent of the present invention.

EXAMPLE 8

The agent of the present invention containing poly(I).poly(C) [mean chain length: about 350 bp] was prepared in the same manner as given in Example 4.

EXAMPLE 9

The agent of the present invention containing poly(I).poly(C) [mean chain length about 1450 bp] was prepared in the same manner as given in Example 4.

EXAMPLE 10

The agent of the present invention containing poly(I).poly(C) [mean chain length: about 80 bp] was prepared in the same manner as given in Example 4.

Test Example 1: β-Interferon Induction Effect in Mouse Liver (In Vivo)

The agent of the present invention according to Example 4 or poly(I).poly(C) alone for control was administered by i.v. injection into 3 male mice (Balb/c, 5-week-old). After 3 hours, the livers were collected and total RNA was extracted by the acid-guanidine-phenol-chloroform (AGPC) method. The amount of expressed β-interferon mRNA was determined by RT-PCR. The result is shown in FIG. 1.

It is apparent from FIG. 1 that every sample expressed β-interferon mRNA and that β-interferon was induced in a dose-depending manner. The agent of present invention induced more β-interferon than the poly (I) poly (C) alone did.

Test Example 2: β-Interferon Induction Effect in Mouse Tissues Other than Liver (In Vivo)

The amount of expressed β-interferon mRNA in mouse tissues other than liver was determined in the same manner as Text Example 1. The result is shown in FIG. 2.

It is apparent from FIG. 2 that the agent of the present invention did not bring about the expression of β-interferon mRNA or the induction of β-interferon very much in the kidney, lung and brain.

The results of Test Examples 1 and 2 above show that poly(I).poly(C) alone is not targeted to any specific tissues but the agent of the present invention induces β-interferon very much in the liver and spleen in particular.

Test Example 3: Amount of Interferon in Mouse Serum (In Vivo)

The agent of the present invention according to Example 4 or poly(I).poly(C) alone for control was administered by i.v. injection into 3 male mice (Balb/c, 5-week-old). After 3 hours, the serum was collected and the interferon level in serum was determined on basis of the inhibitory effect on the degeneration of L929 cells by virus (VSV) infection. The result is shown in Table 1.

TABLE 1

Interferon Level in Mouse Serum

|  | dosage (μg/kg) | Interferon level (IU/ml) |
|---|---|---|
| control | — | <3 |
| Example 4 | 10 | 13 ± 2 |
|  | 30 | 41 ± 1 |
|  | 100 | 63 ± 18 |
| poly(I) · poly(C) | 10 | <3 |
| alone | 30 | 5 ± 2 |
|  | 100 | 18 ± 6 |

It is apparent from Table 1 that interferon was detected in serum in a dose-depending manner in every sample, but more interferon was detected in animals received the agent of the present invention.

In animals of a group which received 100 μg/kg of the agent of the present invention, the interferon level was 63 I.U./ml at 3 hour, and 30 I.U./ml even at 24 hour after the administration. It has been reported that when β-interferon of $3 \times 10^6$ I.U. was administered to human clinically, the plasma level of interferon was 67 I.U./ml immediately after the administration, and was not detected after 45 minutes. Therefore, these results indicate that the agent of the present invention can induce clinically enough amount of β-interferon continuously.

Test Example 4: Toxicity Study (1) Expression of Hepatotoxicity in Rats after a Single Dose (Acute Toxicity Study)

To eight male SD rats aged 6 weeks were intravenously injected the agent of the present invention according to Example 4 in a single dose, and the serum aminoacyl transferase level was determined after 20 hours. As a result, no death was observed at doses up to 5 mg/kg, at which dose a slight elevation of serum aminoacyl transferase at most was observed. At 1 mg/kg, the serum aminoacyl transferase level was little elevated.

(2) Two-Week Limited Subacute Toxicity Study in Rats

The agent of the present invention according to Example 4 was administered intravenously to 6 male SD rats (aged 6 weeks) daily for 14 consecutive days. As a result, no remarkable sign of toxicity was found at doses up to 1 mg/kg.

(3) Antigenicity Study

Using male guinea pigs (Hartley strain, 5 weeks old), the antigenicity of the agent of the present invention according to Example 4 was studied. As a result, no antigenicity was found at 50 μg/animal.

(4) Expedient Mutagenicity Study

The agent of the present invention according to Example 4 was subjected to expedient reverse mutation assay and expedient chromosomal aberration assay. As a result, no mutagenicity was found at 10 μg/ml.

Figure 1:
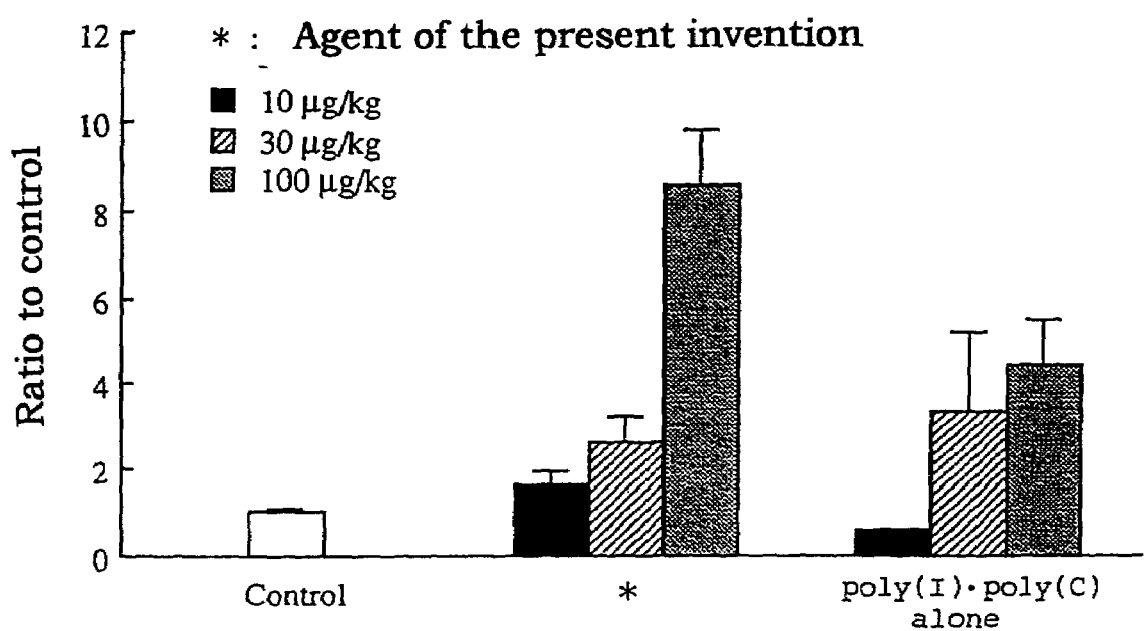
FIG. 1 is a graph showing the amount of β-interferon mRNA expressed in mouse liver. The left end column in the figure represents the control group. The central three columns represent the results obtained in the groups received the agent of the present invention according to Example 4, wherein each column corresponds to a group administered the agent at a dosage of 10 μg/kg, 30 μg/kg, and 100 μg/kg from the left-hand in order. The right end three columns represent the results obtained in the groups received the poly(I).poly(C) preparation alone, wherein each column corresponds to a group administered the preparation at a dosage of 10 μg/kg, 30 μg/kg, and 100 μg/kg from the left-hand in order. The ordinate represents the ratio of the amount of β-interferon mRNA expressed in the drug administration groups to that in control.
Figure 2:
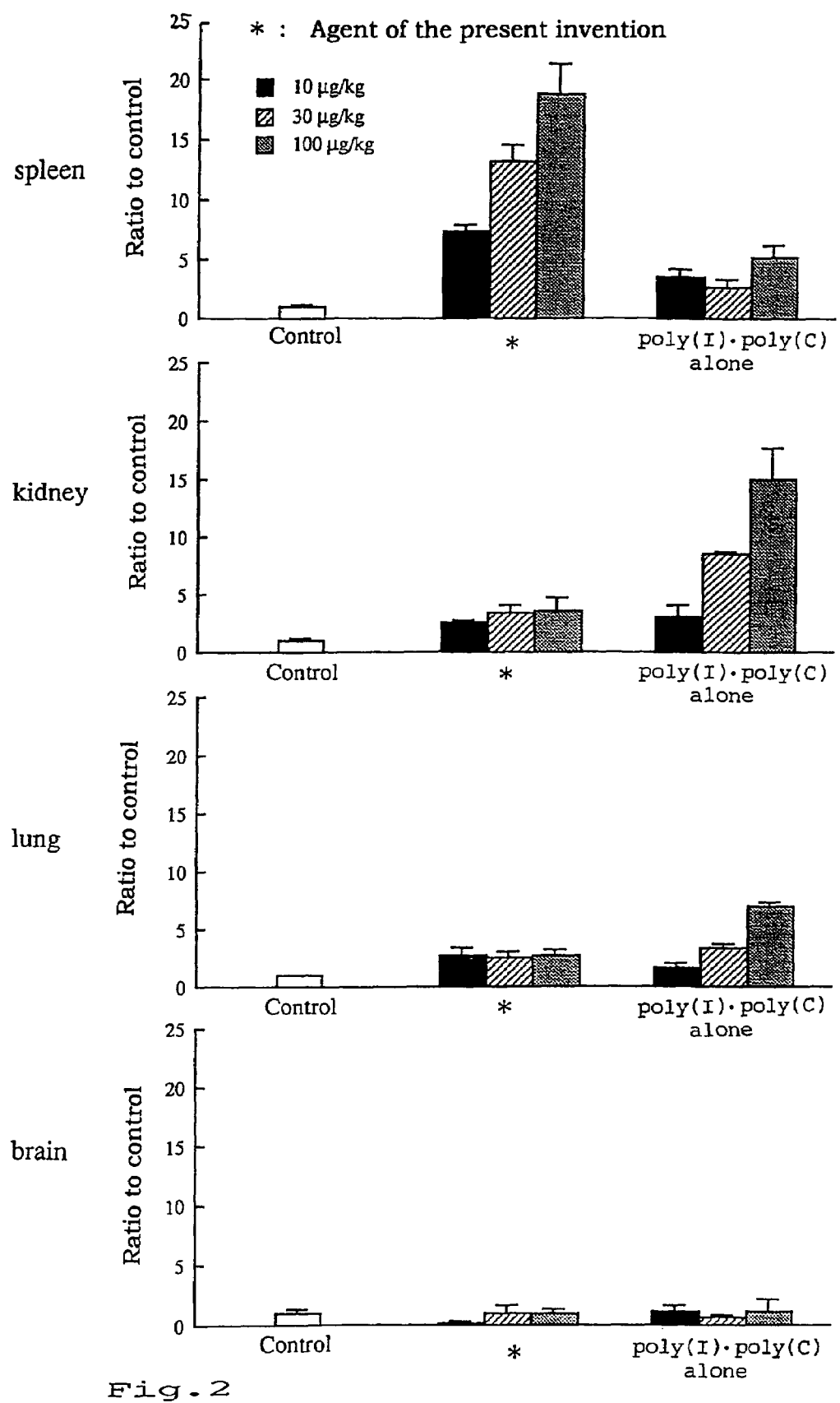
FIG. 2 is a graph showing the amount of β-interferon mRNA expressed in mouse tissues (spleen, kidney, lung, and brain from the top in order). The left end column in each figure represents the control group. The central three columns in the figure for each tissue represent the results obtained in the groups received the agent of the present invention according to Example 4, wherein each column corresponds to a group administered the agent at a dosage of 10 μg/kg, 30 μg/kg, and 100 μg/kg from the left-hand in order. The right end three columns in the figure for each tissue represent the results obtained in the groups received the poly(I).poly(C) preparation alone, wherein each column corresponds to a group administered the preparation at a dosage of 10 μg/kg, 30 μg/kg, and 100 μg/kg from the left-hand in order. The ordinate represents the ratio of the amount of β-interferon mRNA expressed in the drug administration groups to that in control.

The invention claimed is:

1. A method of treating hepatitis C in a human in which interferon is effective comprising the steps of:
   1) intravenously, transmucosally, or hepatic intra-arterially administering to the human a complex of a cationic liposome consisting essentially of 2-O-(2-diethylaminoethyl)carbamoyl-1,3-dioleoylglycerol and a phospholipid, with 1 μg to 50 mg/man per dose of poly(I):poly(C) which has a mean length within the range of 100 to 500 bp once through three times a day, every day, every other day, or on a weekly or fortnightly basis; and
   2) inducing chiefly in the liver an effective amount of interferon.
2. The method according to claim 1, wherein the phospholipid is lecithin.

* * * * *